United States Patent [19]

Koso

[11] Patent Number: 4,801,810
[45] Date of Patent: Jan. 31, 1989

[54] ELLIPTICAL REFLECTOR ILLUMINATION SYSTEM FOR INSPECTION OF PRINTED WIRING BOARDS

[75] Inventor: Dusan A. Koso, Cambridge, Mass.
[73] Assignee: Gerber Scientific, Inc., South Windsor, Conn.
[21] Appl. No.: 73,013
[22] Filed: Jul. 13, 1987
[51] Int. Cl.$^4$ ............................................. G01N 21/88
[52] U.S. Cl. ..................................... 250/572; 250/216; 356/430
[58] Field of Search ....................... 356/430, 431, 237; 250/571, 572, 216

[56] References Cited

U.S. PATENT DOCUMENTS 4,095,905  6/1978  Kuni et al. ............................ 250/572
4,597,665  7/1986  Galbraith et al. ..................... 356/237
4,714,327  12/1987  Marshall ............................... 350/504

Primary Examiner—David C. Nelms
Assistant Examiner—Crystal Cooper
Attorney, Agent, or Firm—Joseph S. Iandiorio; Douglas E. Denninger; Michael L. Sheldon

[57] ABSTRACT

An elliptical reflector illumination system for inspection of printed wiring boards including an elliptical reflector element for mounting above the board to be inspected with a region of the board generally at a first elliptical focus of the reflector element. There is a light source mounted generally at a second elliptical focus of the elliptical reflector element for illuminating substantially all facets of the region of the board at the first focus. One or more detectors are provided for sensing light reflected from the illuminated facets of at least a portion of the illuminated region of the board at the first focus.

18 Claims, 5 Drawing Sheets

ELLIPTICAL REFLECTOR ILLUMINATION SYSTEM FOR INSPECTION OF PRINTED WIRING BOARDS

FIELD OF INVENTION

This invention relates to an elliptical reflector illumination system for inspection of printed wiring boards.

BACKGROUND OF INVENTION

Conventional specular techniques for inspecting printed wiring boards often provide a large number of false indications. In such techniques light is reflected from small regions of the board and the intensity of the reflected light is detected to indicate the presence of copper circuit material or substrate. However, if the flatness of the reflecting surface varies even slightly from what is expected, the light rays may be redirected so that no reflected light reaches the detector. In such cases the detector fails to detect the presence of the reflecting material.

Alternative systems have illuminated the substrate either from below or at a region away from the region to be inspected so that the printed foil creates shadows which indicate its presence. Such systems are typically not successful when used with boards employing large areas of copper which tend to block the light. Moreover, foil provided on the bottom of the board is likely to interfere with lighting from below the board and provide false indications when the top of the board is being viewed.

In one approach a laser has been used to illuminate the substrate at a first wavelength and cause certain substrate materials to fluoresce at a second wavelength. The foil appears as a shadow against the fluorescent substrate. This technique is relatively complicated and requires that fluorescent materials be employed. Such materials affect the chemical composition of the board.

In another relatively complex system the board is placed in a vacuum chamber and an electric field is applied between the circuit material and a transparent electrode spaced above the board. The air between the foil and electrode is ionized to provide a glow indicating the presence of foil.

SUMMARY OF THE INVENTION

It is therefore an object of this invention to provide an elliptical reflector illumination system which permits enhanced inspection of printed wiring boards by providing for strong uniform contrast between the materials being inspected.

It is a further object of this invention to provide an elliptical reflector illumination system for inspection of printed wiring boards which exhibits enhanced uniform detection of radiation reflected from printed wiring boards having surface irregularities.

It is a further object of this invention to provide an elliptical reflector illumination system which provides for effective inspection of printed wiring boards having large areas of copper wiring and/or wiring on both sides of the board.

It is a further object of this invention to provide an elliptical reflector illumination system for inspection of printed wiring boards which does not require fluorescent additives, electric fields, vacuum chambers or other complicated schemes to enhance illumination and which provides such enhanced illumination without the need for a diffuser element.

This invention results from a realization that improved uniform contrast between printed wiring board materials may be achieved regardless of the surface irregularities of those materials by employing an elliptical reflector with a light source mounted proximate one focus and a region of the board to be illuminated proximate the other focus. The region of the board at the focus is illuminated by light from all points on the reflector so that all facets of successive regions are uniformly illuminated.

This invention features an elliptical reflector illumination system for inspection of printed wiring boards which includes an elliptical reflector element for mounting above the board to be inspected with a region of the board generally at a first elliptical focus of the reflector element. There is a light source mounted generally at a second elliptical focus of the elliptical reflector element for illuminating substantially all facets of the region of the board at the first focus. Detector means are provided for sensing light reflected from the illuminated facets of at least a portion of the illuminated region of the board at the first focus.

In a preferred embodiment the reflector element is mounted between the detector means and the board to be inspected and includes aperture means for transmitting light reflected from the board to the detector means. The reflector element is preferably spaced from the board to be inspected.

First optical means may be provided for directing the light reflected from the board to the detector means. Such first optical means may include at least one lens. Second optical means such as a beam splitter may also be provided for directing light from a zone between the detector means and the board to the illuminated region of the board.

The light source may include fluorescent means and filter means may be included between the light source and the reflector element for providing selective wavelengths of light to illuminate the board.

The means for detecting may include at least one charge-coupled device. Means, responsive to the detector means, may be provided for indicating the intensity of the sensed reflected light. Means, responsive to the detector means, may also be provided for comparing the intensity of the sensed reflected light with a reference intensity for the board being inspected. Typically, means responsive to such means for comparing are provided for indicating deviations in the intensity of the sensed reflective light from the reference intensity to denote errors in the board being inspected. Calibration means, responsive to the detector means may be provided for maintaining the intensity of the reflected radiation sensed by the detector means.

Means may be employed for mounting the board to be inspected and means may also be provided for moving one of the light source and the means for mounting to illuminate successive regions of the board.

DISCLOSURE OF PREFERRED EMBODIMENT

Other objects, features and advantages will occur from the following description of a preferred embodiment and the accompanying drawings, in which.

Figure 1:
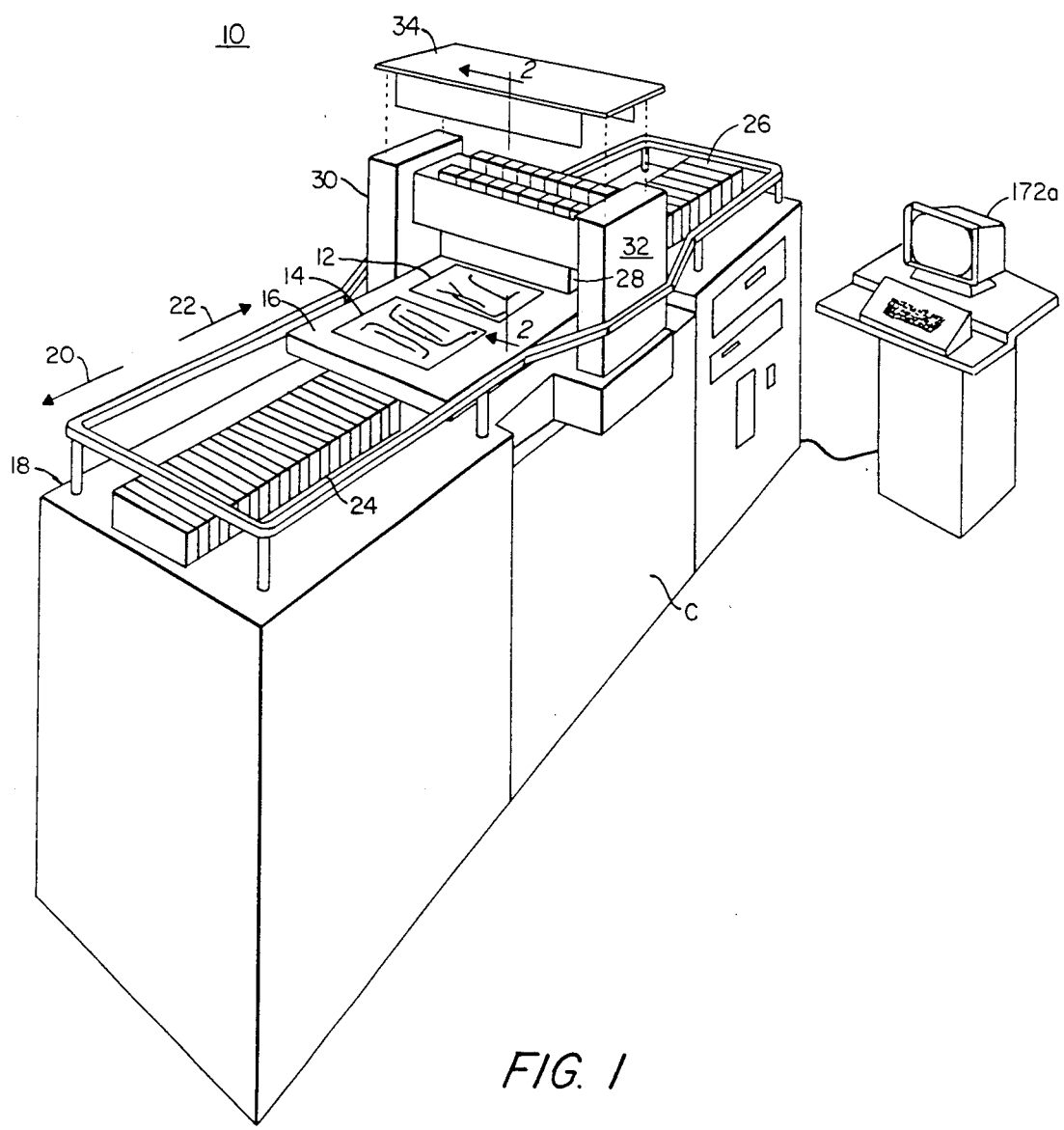
FIG. 1 is an axonometric view of a machine utilizing the illumination system of this invention.

An elliptical reflector illumination system for inspecting printed wiring boards according to this invention may be accomplished with an elliptical reflector element for mounting above the board with a region of the board at a first elliptical focus. A light source is mounted at a second focus of the elliptical reflector for uniformly illuminating substantially all facets of the region of the board at the first focus. Detector means are provided for sensing light reflected from the illuminated facets of the board at the first focus. Preferred light sources include 15 to 20 watt fluorescent bulbs. Incandescent bulbs of a special design, e.g., similar to bulbs used for aquarium or display case lighting but with an 18" long filament, may also be used.

The reflector element is preferably mounted between the detector and the board to be inspected and has aperture means for transmitting light reflected from the board to the detector means. The concave elliptical element typically clears the board by approximately 10 to 15 mils. The aperture means may form a longitudinal slit approximately $\frac{1}{8}$ inch wide in the reflector. A preferred reflector element consists of aluminum, glass or quartz or other mirror materials and has a polished reflector surface.

The detector means may include arrays of charge-coupled devices (CCDs). A typical detector means includes twelve to twenty one-inch detectors, each mounted in a 1½ inch frame and including 2,048 CCDs. Each detector senses a section of a very thin (e.g., one-half mil) portion within an illuminated board region approximately 5 to 10 mils wide. A typical strip of copper track or foil material on the board is between 6 and 20 mils wide. The reflected radiation is directed first through the slit in the elliptical reflector to the CCDs by lens and mirror systems.

To reduce the effects of blind spots caused when the detector encounters a perpendicular flat upper surface of the board, the slit in the reflector element may be disposed at an angle (e.g., 45°) relative to the plane of the board. Alternatively, a beam splitter may be employed to provide light to the board from the zone between the detector and normal surfaces of the board.

To inspect printed wiring boards for errors the boards are mounted on a movable single axis table such as is provided by Anorad Corp. The board is moved beneath the light source and detector means so that successive regions of the board are illuminated and inspected.

A signal indicative of the detected reflected intensity may be employed to determine the material being detected. It may also be compared with a reference intensity for the board being inspected. Deviations of the sensed reflective light from the reference intensity are used to denote errors in the test board. To normalize the intensity of the reflected radiation sensed by the detector means and to eliminate the effects of uneven lighting, a calibration system is provided.

This system may be employed at a number of stages in the production of printed wiring boards. The wavelengths of light used to inspect the boards at various stages are chosen to maximize the contrast between respective materials on the board and are selected by employing appropriate filters with the light source. For example, during the photomaster art work stage white light is used to inspect the board. Such light provides a black and white contrast between the substrate and track material respectively. During the sepia process light is provided at between 3500 Angstroms and 5500 Angstroms. This provides the required contrast between the background material and the sepia traces. Following development, with a photoresist layer applied over copper, green, red or blue reflected light indicates the photoresist material whereas a reddish color indicates the copper. Following reflow of solder over copper, white light is utilized to provide a contrast between solder and substrate, respectively. These examples are given for illustrative purposes only and should not be taken to limit this invention.

There is shown in FIG. 1 a machine 10 for inspecting printed wiring boards 12 and 14. The boards are mounted as more fully described in FIG. 2 to movable platform 16 which is a part of a single axis table 18. Platform 16 is driven in the direction of arrows 20 and 22 by drive mechanisms 24 and 26. Typically the platform is permitted to move approximately 22 inches and during that movement printed wiring boards 12 and 14 are passed beneath an optical head 28 which contains most elements of the illumination system of this invention. Head 28 is held above table 18 by supports 30 and 32 and is covered by a plate 34.

Figure 2:
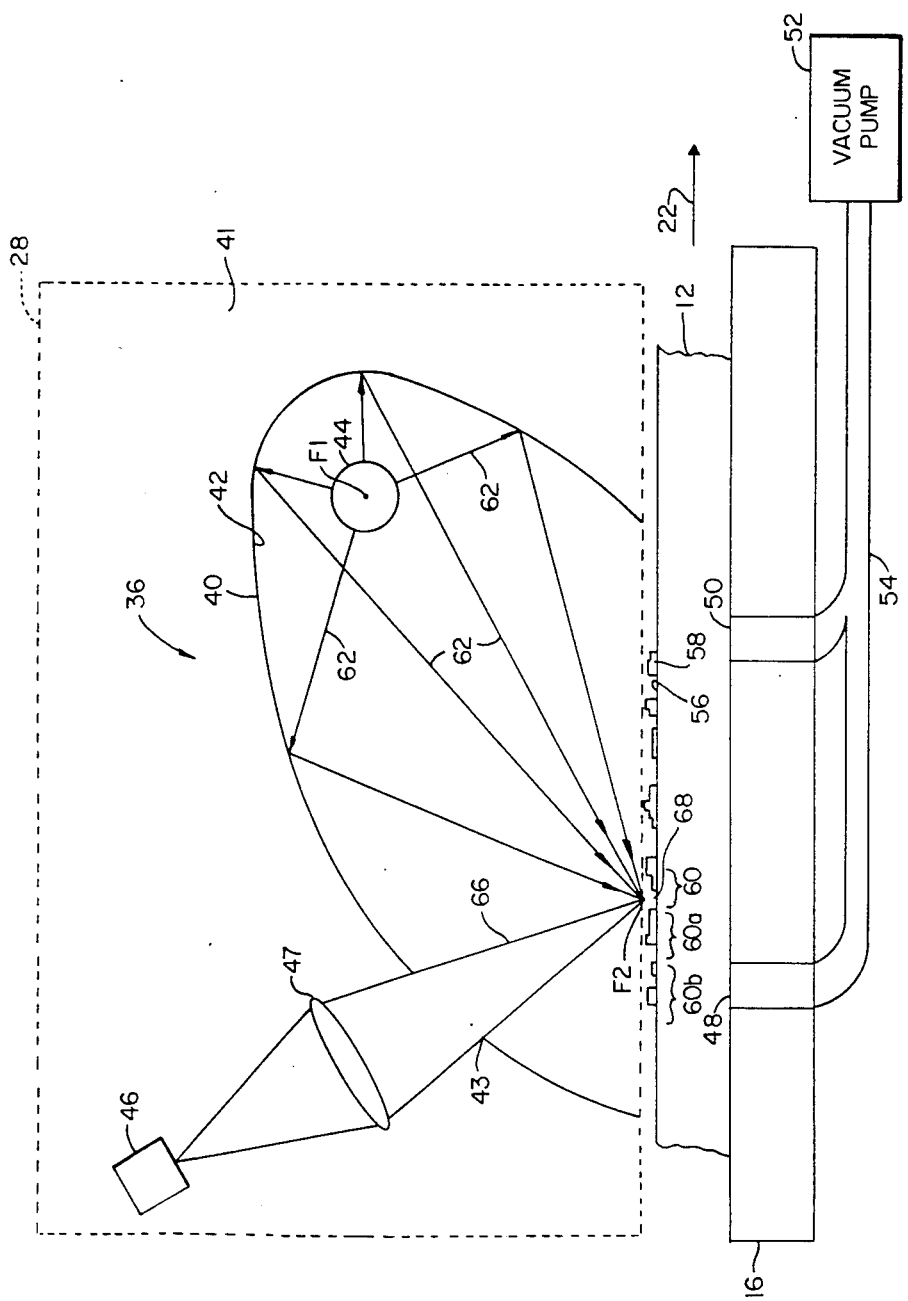
FIG. 2 is a cross sectional partly schematic view taken along line 2—2 of FIG. 1 of a preferred illumination system according to this invention.
Figure 3:
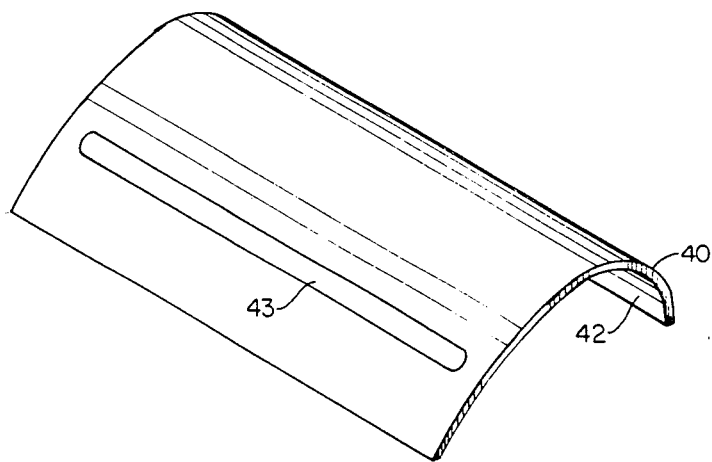
FIG. 3 is an axonometric view of the elliptical reflector.

As shown in FIG. 2 illumination system 36 is mounted within head 28 and includes a concave reflector element 40, FIG. 3, mounted by brackets or any other suitable means of attachment, not shown, between end walls 41, only one of which is shown, of head 28 and having an elliptical cross section and a polished reflective inner surface 42. Reflector element 40 also includes a narrow longitudinal aperture 43 located at an angle of approximately 45° relative to the bottom of head 28. An elongate fluorescent light source 44 is likewise mounted to end walls 41 of head 28. Light source 44 is arranged generally at a focus F1 of reflector 40 and extends generally parallel to the reflector. A plurality of detectors 46 and associated lenses 47, only one pair of which is shown, are aligned side-by-side and mounted within head 28 above reflector 40.

Platform 16 includes a plurality of holes such as 48 and 50. A vacuum pump 52 attached to these holes via conduit 54 is activated to draw board 12 downwardly and secure it to platform 16. The top surface of board 12 includes both substrate 56 and track material 58. Head 28 is positioned so that a region 60 of board 12 is generally at the other focus F2 of reflector 40.

In operation platform 16 transports printed wiring board 12 beneath head 28 in the direction of arrow 22. Light rays 62 of desired wavelengths from source 44 are reflected from respective points of surface 42 and focused at F2 along a line that is parallel to source 44 and reflector 40. As a result region 60 is diffusely illuminated by light reflected, and appearing to emanate uniformly from, all points on the reflective elliptical surface 42. This causes all facets of board 12 within region 60 to be uniformly illuminated. Reflected light 66 from a portion 68 of the illuminated region 60 of board 12 is transmitted through aperture 43 to lenses 47 which direct the light to detectors 46 where the intensity of reflected radiation 66 is sensed. As the board moves in the direction of arrow 22 successive regions 60a, 60b, etc. are illuminated and light reflected from successive portions is detected.

Figure 4:
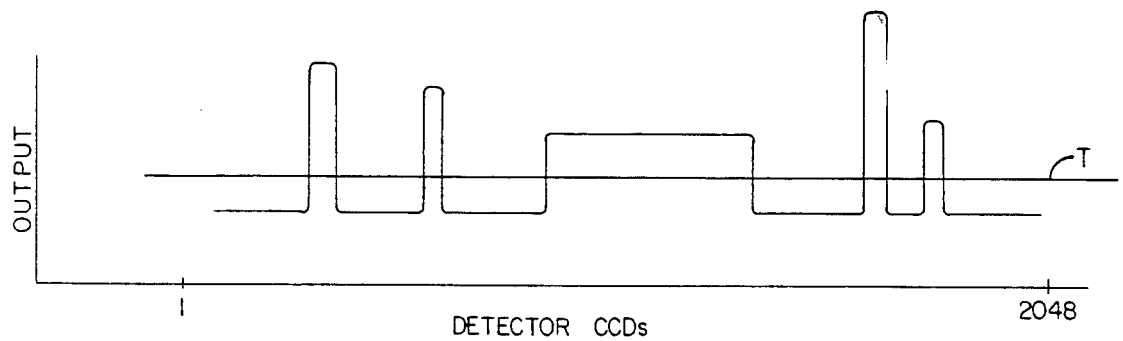
FIG. 4 is a representative intensity signal provided by a detector to indicate the presence of track and substrate material.

Typically, each detector 46 includes an array of, for example, 2,048 charge-coupled devices (CCDs). As shown in FIG. 4, the output of a typical detector 46 comprises the output of all of that detector's 2,048 CCDs. That output is a function of intensity of the light reflected from the board and sensed by each of the CCDs. When that intensity rises above a threshold level T, a high degree of reflection is detected which indicates the presence of track material. However, when the intensity and therefore the output of the detector drops below threshold T, the reflection level is low and substrate material is indicated.

Figure 5:
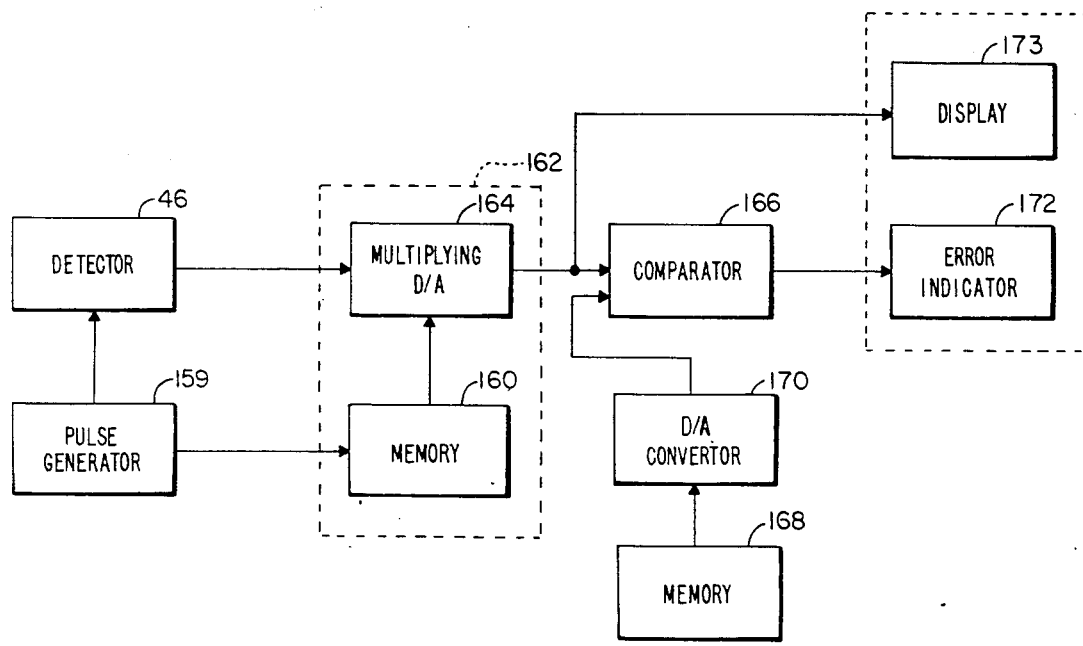
FIG. 5 is a schematic diagram of a circuit for displaying the intensity of the sensed reflected radiation and comparing that intensity with a reference signal to indicate errors in the printed wiring board.

As shown in FIG. 5, clock pulses are provided by pulse generator 159 to each detector 46 and to memory 160 of calibration unit 162. Prior to inspecting a particular board or boards, the system may be calibrated to compensate for slightly varying levels of illumination in the following manner. The intensity sensed by each CCD from a reference board having, for example, only substrate material on its upper surface is multiplied by an appropriate coefficient so that all of the sensed intensities are equal. These 2048 calibrated coefficients are entered into memory 162. In response to inspection of a test board, detector 46 provides an output, FIG. 4, and the output for each CCD is multiplied by its associated coefficient in multiplying D/A converter 164. This normalizes the intensity of the reflected radiation sensed by each detector and compensates for any unevenness in the intensity of the light illuminating the board. The calibrated signal is then provided to a comparator 166 where it is compared with a reference signal stored in memory 168 and converted to an analog signal by D/A converter 170. Any deviation in the calibrated signal from the reference signal is denoted by error indicator 172. A typical indicator includes CRT display 172a, FIG. 1, which indicates the presence, type and location of defects in the scanned board.

By locating aperture 43 at an acute angle relative to the plane of board 12, FIGS. 2, 3, system 36 significantly reduces blind spots. These are experienced when a detector directly confronts a flat or perpendicular surface of the board (e.g., when the detector is disposed along a perpendicular line from the surface of the board). The amount of board surface which the detector confronts in this manner and the extent of blind spots experienced when the detector is located at the acute angle of FIG. 2 is relatively slight.

Figure 6:
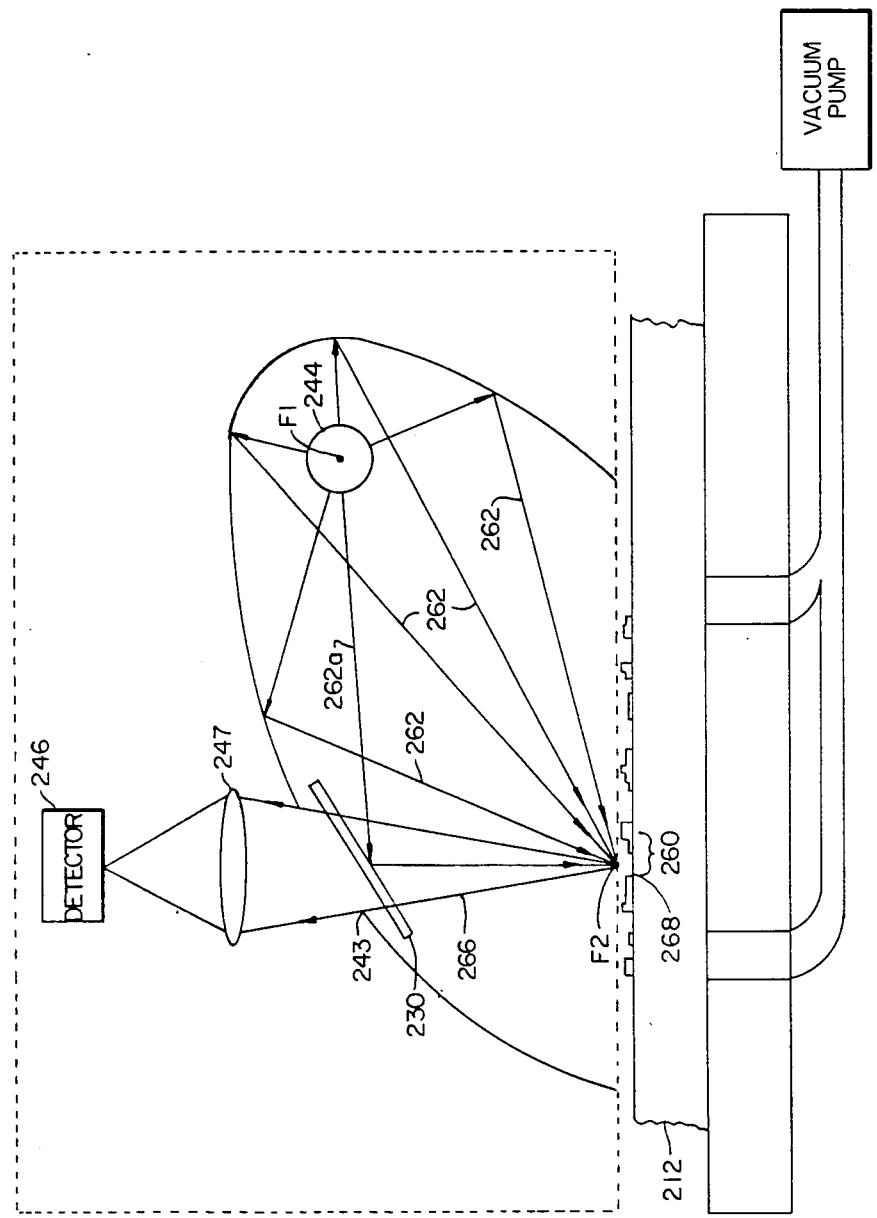
FIG. 6 is a simplified partly schematic cross-sectional view of an alternative embodiment which employs a beam splitter for reducing the effect of retroreflection.

Alternatively, blind spots may be reduced, as shown in FIG. 6, by placing detectors 246 along the normal to board 212 and employing a beam splitter 230 which is mounted between each detector 246 and board 212. Light 262 from source 244 is largely reflected by reflector 240 to diffusely illuminate board region 260 at focus F2. A portion 262a of the light is likewise reflected from beam splitter 230 and directed to illuminate region 260. Reflected diffuse light 266 from portion 268 of illuminated region 260 of board 212 is transmitted through beam splitter 230 and opening aperture 243 in reflector 240. The light is then directed by lens 247 to detector 246. Enhanced uniform illumination of the board is provided and blind spots are greatly reduced.

In still other embodiments the blind spots may be reduced by mounting the detector slightly off of the optical axis through lens 247.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. An elliptical reflector illumination system for inspection of printed wiring boards comprising:
    an elliptical reflector element for mounting above the board to be inspected with a region of said board generally at a first elliptical focus of said reflector element;
    a light source mounted generally at a second elliptical focus of said elliptical reflector element for illuminating substantially all facets of said region of the board at the first focus; and
    detector means for sensing light reflected from the illuminated facets of at least a portion of the illuminated region of the board at the first focus.

2. The illumination system of claim 1 in which said reflector element is mounted between said detector means and the board to be inspected and includes aperture means for transmitting light reflected from the board to said detector means.

3. The illumination system of claim 1 in which said reflector element is spaced from the board to be inspected.

4. The illumination system of claim 1 in which said detector means includes at least one charge-coupled device.

5. The illumination system of claim 1 further including first optical means for directing the light reflected from said board to said detector means.

6. The illumination system of claim 5 in which said first optical means includes at least one lens.

7. The illumination system of claim 1 further including second optical means for directing light from a zone between said detector means and the board to the illuminated region of the board.

8. The illumination system of claim 7 in which said second optical means includes a beam splitter.

9. The illumination system of claim 1 further including means for mounting the board to be inspected.

10. The illumination system of claim 1 further including means for moving one of said light source and said means for mounting to illuminate successive regions of the board.

11. The illumination system of claim 1 in which said light source includes fluorescent means.

12. The illumination system of claim 1 further including filter means between said light source and said reflector element for providing selected wavelengths of light to illuminate said board.

13. The illumination system of claim 1 in which white light is provided by said light source for illuminating said board in the photomaster artwork stage.

14. The illumination system of claim 1 further including means, responsive to said detector means, for indicating the intensity of the sensed reflected light.

15. The illumination system of claim 1 further including means, responsive to said detector means, for comparing the intensity of the sensed reflected light with a reference intensity for the board being inspected.

16. The illumination system of claim 15 further including means, responsive to said means for comparing, for indicating deviations of the intensity of the sensed reflected light from the reference intensity to denote errors in the board being inspected.

17. The illumination system of claim 1 further including calibration means, responsive to said detection means, for maintaining the intensity of the reflected radiation sensed by said detector means.

18. An elliptical reflector illumination system for inspection of printed wiring boards comprising:
 means for mounting a board to be inspected;
 an elliptical reflector element for mounting above the board to be inspected with a region of the board generally at a first elliptical focus of said reflector element;
 a light source mounted generally at a second elliptical focus of said elliptical reflector element for illuminating substantially all facets of said region of the board at the first focus;
 detector means for sensing light reflected from the illuminated facets of at least a portion of the illuminated region of the board; and
 means for moving said means for mounting to illuminate at the first focus successive regions of the board.

* * * * *